United States Patent [19]

Lacivita

[11] Patent Number: 5,554,131

[45] Date of Patent: Sep. 10, 1996

[54] HYPODERMIC NEEDLE WITH PROTECTION DEVICE

[75] Inventor: Antonio Lacivita, Turin, Italy

[73] Assignee: Pia Carpinelli, Cumiana, Italy

[21] Appl. No.: 199,162

[22] PCT Filed: Jun. 22, 1993

[86] PCT No.: PCT/EP93/01619

§ 371 Date: May 24, 1994

§ 102(e) Date: May 24, 1994

[87] PCT Pub. No.: WO94/01152

PCT Pub. Date: Jan. 20, 1994

[30] Foreign Application Priority Data

Jul. 13, 1992 [IT] Italy .................. TO92A0579

[51] Int. Cl.$^6$ ............................................. A61M 5/32
[52] U.S. Cl. ................ 604/198; 604/110; 604/263
[58] Field of Search ............................ 604/110, 192, 604/198, 263, 162, 167

[56] References Cited

U.S. PATENT DOCUMENTS

| 4,725,267 | 2/1988 | Vaillancourt | 604/192 |
| 4,728,321 | 3/1988 | Chen | 604/110 |
| 5,232,454 | 8/1993 | Hollister | 604/192 |
| 5,232,455 | 8/1993 | Hollister | 604/192 |

FOREIGN PATENT DOCUMENTS

| 0409180 | 1/1991 | European Pat. Off. |
| 0414536 | 2/1991 | European Pat. Off. |
| 8910767 | 11/1989 | WIPO |
| 9401152 | 1/1994 | WIPO |

*Primary Examiner*—John D. Yasko
*Assistant Examiner*—Ronald K. Stright, Jr.
*Attorney, Agent, or Firm*—Renner, Otto, Boisselle & Sklar

[57] ABSTRACT

A hypodermic needle provided with a protection device against infection risks, substantially comprising a cap (1), or a hollow member shaped like a cylinder or a truncated cone, with piercing-resistant walls (3) having an inner irregular profile (5), which member can be snap-secured to the base (7) supporting the needle (9), and provided at its base (7) with a resilient element (13) formed like a coil or sheath and exhibiting a marked propelling capability, and with a preferably eccentric hole (17) at the tip (15) thereof.

2 Claims, 3 Drawing Sheets

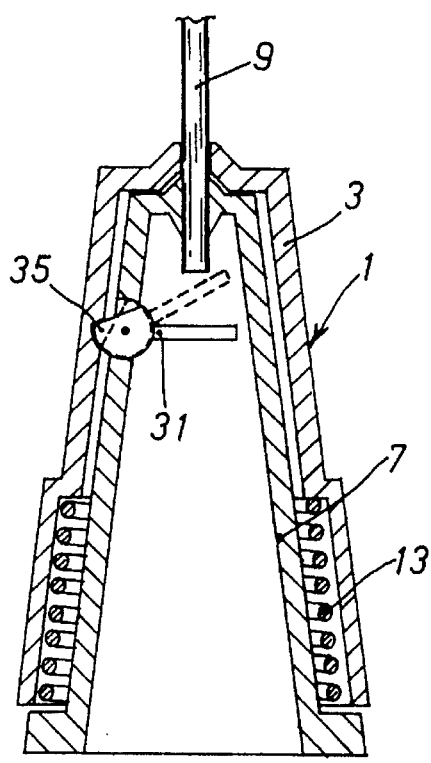
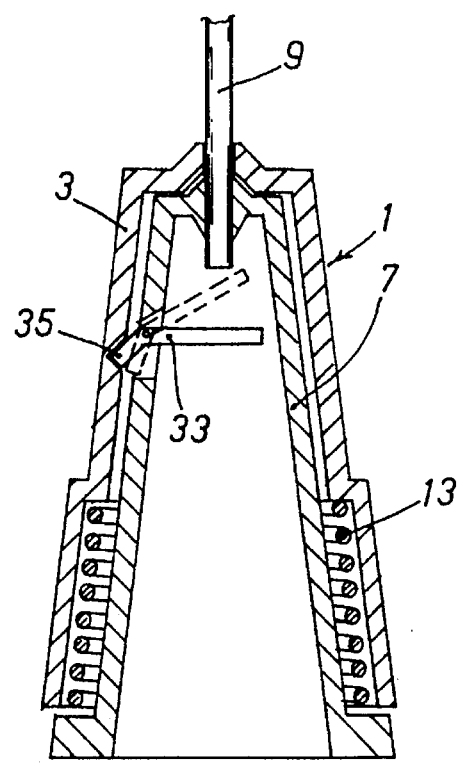
FIG.5  FIG.6
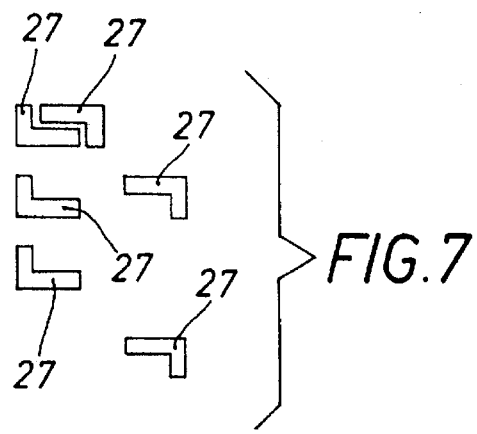
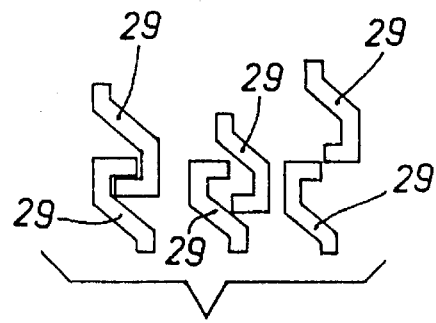
FIG.7  FIG.8

HYPODERMIC NEEDLE WITH PROTECTION DEVICE

BACKGROUND OF THE INVENTION

1. Field of the Invention

The present invention relates to a hypodermic needle with a device for protecting against the risks of infection.

2. Description of the Related Art

It is known that the presently used hypodermic needles for sanitary use have not substantially changed compared with the commonly known type.

As a matter of fact some attempts have been carried out in order to prevent the needle from infecting a handler after the use of the hypodermic needle, but in practice they did not get the success they perhaps deserved, so that things are still in the well known initial state.

The only true realty is that at present in almost all cases disposable syringes and needles are used, i.e. adapted for just one use and properly protected before their using by suitably sterilised packagings, but not protected after use.

SUMMARY OF THE INVENTION

An object of the present invention is to overcome this drawback by providing a hypodermic needle which is easy and practical to be used and nevertheless equipped with an effective device for the protection against infection.

The protection device substantially comprises a cap or a hollow member having a cylindrical or truncated cone shape, with piercing-resistant walls having an inner irregular profile snap-secured to a base supporting the needle, and provided at its base with a resilient element formed like a coil or sheath with a marked propelling capability, and at the other end with a preferably eccentric hole.

Within the cap cavity there is provided a pocket, outwardly defined by the cap walls and inwardly by a pierceable metal foil, with such pocket containing an adhesive and air-hardening material, in case supported by a resilient spongy material.

Said adhesive and hardening material is to be understood as comprising a physical-chemical composition adapted to envelop the portion of the needle stuck thereinto after use, which occludes the hole and sets very quickly, so as to render the hypodermic needle no longer separable from the protection cap.

Said snap engagement of the cap to the needle supporting base provides three main different embodiments of the invention: a first manually operated one; a second which is semi-automatic; and a third one which is a fully automatic and actually preferred embodiment.

According to the first embodiment, the cap is locked onto the needle base by a series of cooperating snap retainers located on the inner wall of the cap and on the outer wall of the needle base mating the cap: a short manually imparted displacement of the cap causes the cap to be released from the base, and allows it to spring upward to wholly shelter the needle. It is to be understood that said displacement can even be imparted with the needle still inserted in the skin, so that the cap is released and springs forward to shelter the exposed portion of the needle 9, and remains ready to wholly cover it, as soon as it will be extracted from the skin.

According to the second embodiment, the cap is retained by the needle base through a series of retainers provided with an inclined surface: the pressure applied by the skin to the needle cap while pricking lowers said cap with respect to its mating base, causing said locks to slide along said inclined surfaces, so that the cap is rotated with respect to the base and it is disengaged from said base. In said case, the sheltering of the needle by the cap is ensured after the prick has been executed.

According to the third and actually preferred embodiment of the invention, the cap is linked to the base of the needle by a lever device, pivotally secured to the wall of the base and cooperating with a recess in the wall of the cap; as soon as the needle is inserted into the skin, the fluid displaced by the syringe piston acts upon said lever element and causes it to rotate enough to disengage it from the recess provided in the cap, thus allowing the action of the cap propelling means.

BRIEF DESCRIPTION OF THE DRAWINGS

The present invention will be now described with details with particular reference to the accompanying drawings, that are supplied as non limiting examples, in which:

FIG. 5 is an axial cross-section of the cap pertaining to an automatic-snap embodiment;

FIG. 6 is another axial section of the cap in accordance with another automatic-snap embodiment;

FIG. 7 is a diagram of the snap device for the manually operated system;

FIG. 8 is a diagram of the snap device for the semiautomatic system;

DESCRIPTION OF THE PREFERRED EMBODIMENTS

Figure 4:
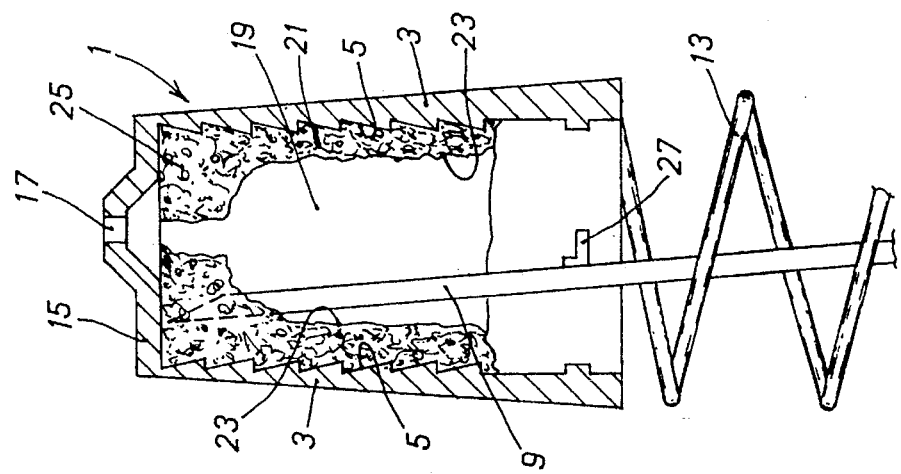
FIG. 4 is a scrap side elevation view of the cross-sectioned cap showing some of its features.
Figure 3:
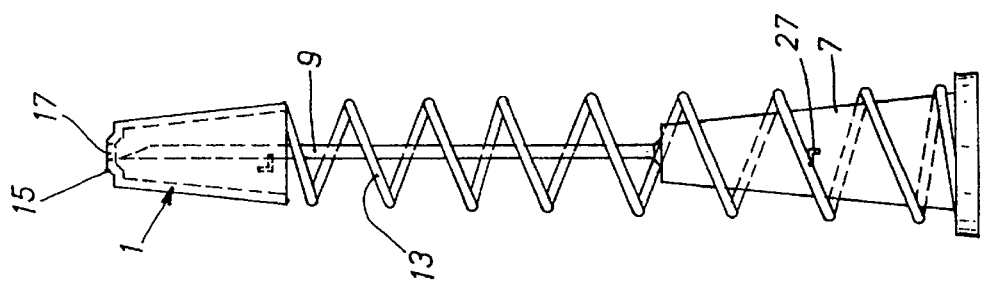
FIG. 3 is a side elevation view of a needle in accordance with the invention with the protection device in its extended position.
Figure 2:
FIG. 2 is a side elevation view of a needle in accordance with the invention with the protection device in its retracted position.
Figure 1:
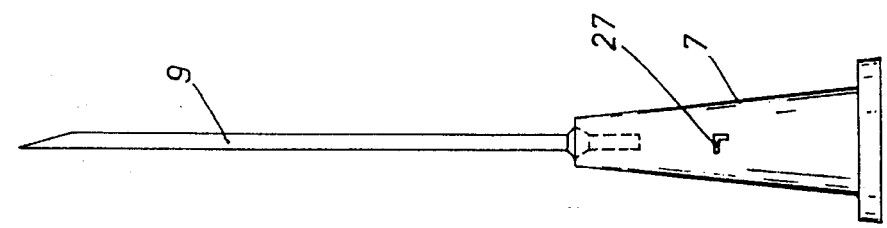
FIG. 1 is a side elevation view of a hypodermic needle without the protection cap.

As clearly shown in the Figures, the subject protection device of hypodermic needles for preventing infections substantially comprises a cap or hollow member shaped like a truncated cone, with piercing-resistant walls 3, having an inner irregular profile 5, which member can be snap-secured to a base 7 supporting the needle 9, and provided at its base 7 with a resilient element 13 formed like a coil or sheath, and exhibiting a marked propelling capability, and with a preferably eccentric hole 17 at the tip 15 thereof.

Inside the cavity 19 of the cap 1 there is provided a pocket 21, outwardly defined by the cap walls 3 and inwardly by a pierceable metal foil 23, with such pocket containing an adhesive and air-hardening material 25, in case supported by a resilient spongy material.

This adhesive and air-hardening material 25 is to be understood as comprising a physical-chemical composition adapted to envelop the portion of the needle 9 stuck thereinto after use, which occludes the hole and sets very quickly, so as to render the hypodermic needle 9 no longer separable from the protection cap 1.

Said snap engagement of the cap 1 to the base 7 supporting the needle 9 provides three substantial different embodiments of the invention: the first is a manually operated one; the second is a semi-automatic one; and the third is a fully automatic and actually preferred embodiment.

According to the first embodiment, the cap 1 is locked onto the needle base 7 by a series of cooperating snap retainers 27 (see FIG. 7) shaped like an upturned L, located on the inner wall of the cap 1 and on the outer wall of the needle base 7 matins the cap 1: a short manually imparted displacement of the cap 1 causes the cap to be released from the base 7, and allows it to spring upward to wholly shelter the needle 9.

FIG. 7 illustrates a sequence of the different retainer positions, respectively in a locked cap condition, in an unlocked cap condition and then in a completely released condition.

It is to be understood that the displacement can be imparted with the needle 9 still inserted in the skin, so that the cap 1 is released and springs forward to shelter the exposed portion of the needle 9, and remains ready to wholly cover it, as soon as it will be extracted from the skin.

According to the second embodiment, the cap 1 is retained by the needle base 7 through a series of retainers 29 (see FIG. 8), provided with an inclined surface: the pressure applied by the skin to the needle cap 1 while pricking lowers said cap 1 with respect to its mating base 7, causing said locks to slide along said inclined surfaces, so that the cap 1 is rotated with respect to the base 7 and it is disengaged from said base. In this case, the sheltering of the needle by the cap I is ensured after the prick has been executed.

FIG. 8 illustrates a sequence of the different retainer positions, respectively in a locked cap condition, in an unlocked cap condition and then in a completely released condition.

According to the third and actually preferred embodiment of the invention shown by FIGS. 5 and 6, the cap 1 is linked to the base 7 of the needle 9 by a lever device 31 or 33, pivotally secured to the wall of the base 7 and cooperating with a housing recess 35 in the wall 3 of the cap 1; as soon as the needle 9 is inserted into the skin, the fluid displaced by the syringe piston acts upon said lever element 31 or 33 and causes it to rotate enough to disengage it from the recess 35 provided in the cap, thus allowing the action of the cap propelling means 13.

Figure 9:
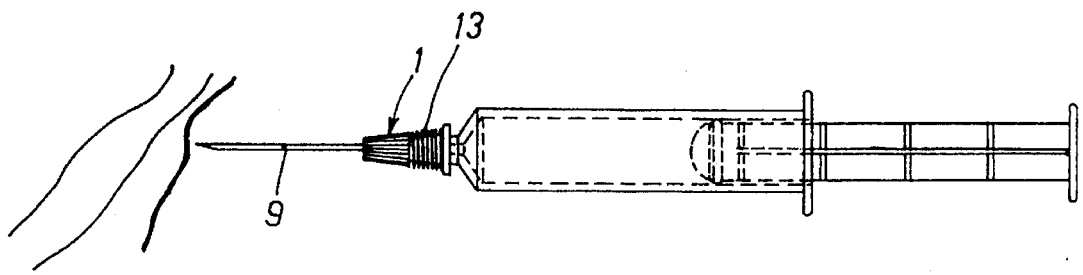
FIG. 9 is a schematic side elevation view of the needle with the protection device before the insertion into the skin.
Figure 10:
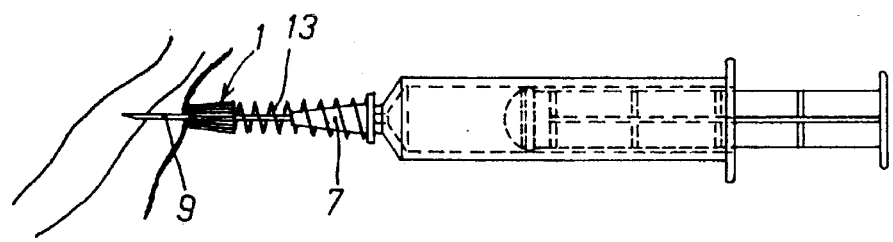
FIG. 10 is a view similar to FIG. 9 showing the needle with the associated protection device just inserted into the patient's skin.
Figure 11:
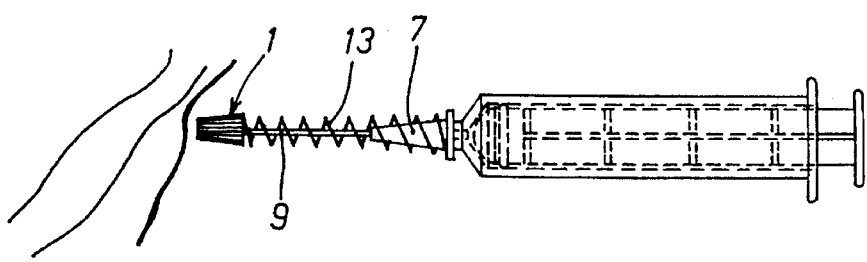
FIG. 11 is a view similar to FIGS. 9 and 10, showing the needle with the protection device just extracted from the patient's skin.

In FIGS. 9, 10 and 11 there are schematically illustrated the steps of a pricking carried out with a needle 9 equipped with the protection device shown by FIGS. 5 and 6.

FIG. 9 clearly shows the needle 9 and the associated protection device 1 locked together with the spring 13 compressed.

As soon as the pricking begins (FIG. 10) and the piston moves, the lever device 31 or 33 becomes disengaged thanks to the flow of the liquid inside the syringe, so that the device 31 or 33 snaps and releases the spring 13 which in turn causes the cap 1 to shift forward until it abuts against the patient's skin.

At the end of the pricking (FIG. 11) the needle 9 is extracted from the skin and the spring 13 urges the cap 1 to completely shelter the piercing tip of the needle 9.

I claim:

1. A hypodermic needle with an after-use protection device against infection risks, comprising a cap (1) or a hollow member having a cylindrical or truncated cone shape, with piercing-resistant walls (3) having an inner irregular profile (5), a base (7) and said cap being snap-secured to the base (7) supporting the needle (9), and provided at its base (7) with a resilient element (13) with a marked propulsive capability, and at the other end (15) with a preferably eccentric hole (17), wherein inside the cavity (19) of the cap (1) there is provided a pocket (21), outwardly defined by the cap walls (3) and inwardly by a pierceable metal foil (23), said pocket containing an adhesive and air-hardening material (25), in case supported by a resilient spongy material, and wherein the cap (1) is locked to the base (7) of the needle, by a series of cooperating snap retainers (27) located on the inner wall of the cap (1) and on the outer wall of the needle base (7) mating the cap (1) whereby a short manually imparted displacement of the cap (1) causes the cap to be released from the base (7), and allows it to spring upward to wholly shelter the needle (9), with said displacement that can be imparted even with the needle (9) still inserted in the skin, so that the cap (1) is released and springs forward to shelter the exposed portion of the needle (9), and remains ready to wholly cover it, as soon as it will be extracted from the skin.

2. A hypodermic needle with an after-use protection device against infection risks, characterized in that it comprises a cap (1) or a hollow member having a cylindrical or truncated cone shape, with piercing-resistant walls (3) having an inner irregular profile (5), a base (7), and said cap being snap-secured to the base (7) supporting the needle (9), and provided at its base (7) with a resilient element (13) with a marked propulsive capability, and at the other end (15) with a preferably eccentric hole (17) wherein the cap (1) is linked to the base (7) of the needle (9) by a lever device (31 or 33), pivotally secured to the wall of the base (7) and cooperating with a recess (35) in the wall (3) of the cap (1) whereby as soon as the needle (9) is inserted into the skin, the fluid displaced by the syringe piston acts upon said lever element (31, 33) and causes it to rotate enough to disengage it from the recess (35) provided in the cap (1), thus allowing the action of the cap propulsion means (13).

* * * * *